US00PP24647P3

(12) United States Plant Patent
Schoone

(10) Patent No.: US PP24,647 P3
(45) Date of Patent: Jul. 15, 2014

(54) *PHALAENOPSIS* ORCHID PLANT NAMED 'VENTURA'

(50) Latin Name: ***Phalaenopsis* hybrid**
Varietal Denomination: Ventura

(75) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 114 days.

(21) Appl. No.: 13/506,394

(22) Filed: Apr. 17, 2012

(65) Prior Publication Data

US 2012/0272417 P1 Oct. 25, 2012

Related U.S. Application Data

(60) Provisional application No. 61/478,781, filed on Apr. 25, 2011.

(30) Foreign Application Priority Data

Apr. 27, 2011 (NL) ..... PBR OPS798

(51) Int. Cl.
*A01H 5/00* (2006.01)
*A01H 5/02* (2006.01)

(52) U.S. Cl.
CPC ..... *A01H 5/02* (2013.01)
USPC ..... Plt./311

(58) Field of Classification Search
CPC ..... A01H 5/00; A01H 5/02
USPC ..... Plt./311
See application file for complete search history.

*Primary Examiner* — Wendy C Haas
(74) *Attorney, Agent, or Firm* — Foley & Lardner LLP

(57) ABSTRACT

A new and distinct *Phalaenopsis* plant named 'Ventura' particularly characterized by flowers which are green/yellow with a white mark in the middle; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis* hybrid.

Variety denomination: 'Ventura'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Ventura'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Ventura' is a product of a controlled breeding program conducted by the inventors, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Ventura' originated from a cross made by the inventor in 1998 in Strengweg, Heemskerk, The Netherlands. The female or seed parent is the *Phalaenopsis* cultivar designated 'Golden Sun', unpatented. The male or pollen parent is the *Phalaenopsis* cultivar designated 'Sara Lee', unpatented. The new *Phalaenopsis* 'Ventura' was discovered and selected by the inventor as a single flowering plant within the progeny of the stated cross in a controlled environment in 2006 in Strengweg, Heemskerk, The Netherlands.

Asexual reproduction of the new *Phalaenopsis* cultivar by tissue culture (mericloning) was first performed in November, 2006 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Ventura', which in combination distinguish this *Phalaenopsis* as a new and distinct cultivar:

1. flowers which are green/yellow with a white mark in the center;
2. plant produces more than one inflorescence;
3. plants may be propagated economically and uniformly using tissue culture;
4. inflorescence is long and sturdy; and
5. relatively short, dark-green foliage.

In comparison with the parental cultivars of 'Ventura' the female parent 'Golden Sun' has yellow/green flowers, the male parent 'Sara Lee' has bronze/yellow colored flowers, whereas the flowers of 'Ventura' are green/yellow with a white mark in the center.

Presently, the commercial cultivar to which 'Ventura' can be meaningfully compared is the *phalaenopsis* orchid 'Golden Dawn' (unpatented). The color of the flowers of 'Golden Dawn' is also green/yellow, only lighter than the color of the flowers of 'Ventura'. Also the raceme of 'Ventura' is longer and its flowers are a little larger than the raceme and flowers of 'Golden Dawn'.

BRIEF DESCRIPTION OF THE PHOTOGRAPHS

The accompanying photographs illustrate the overall appearance of the new *Phalaenopsis* 'Ventura' showing the colors as true as is reasonably possible with colored reproductions of this type. Colors in the photographs may differ slightly from the color values cited in the detailed botanical description, which accurately describe the color of 'Ventura'.

DETAILED BOTANICAL DESCRIPTION

Figure 1:
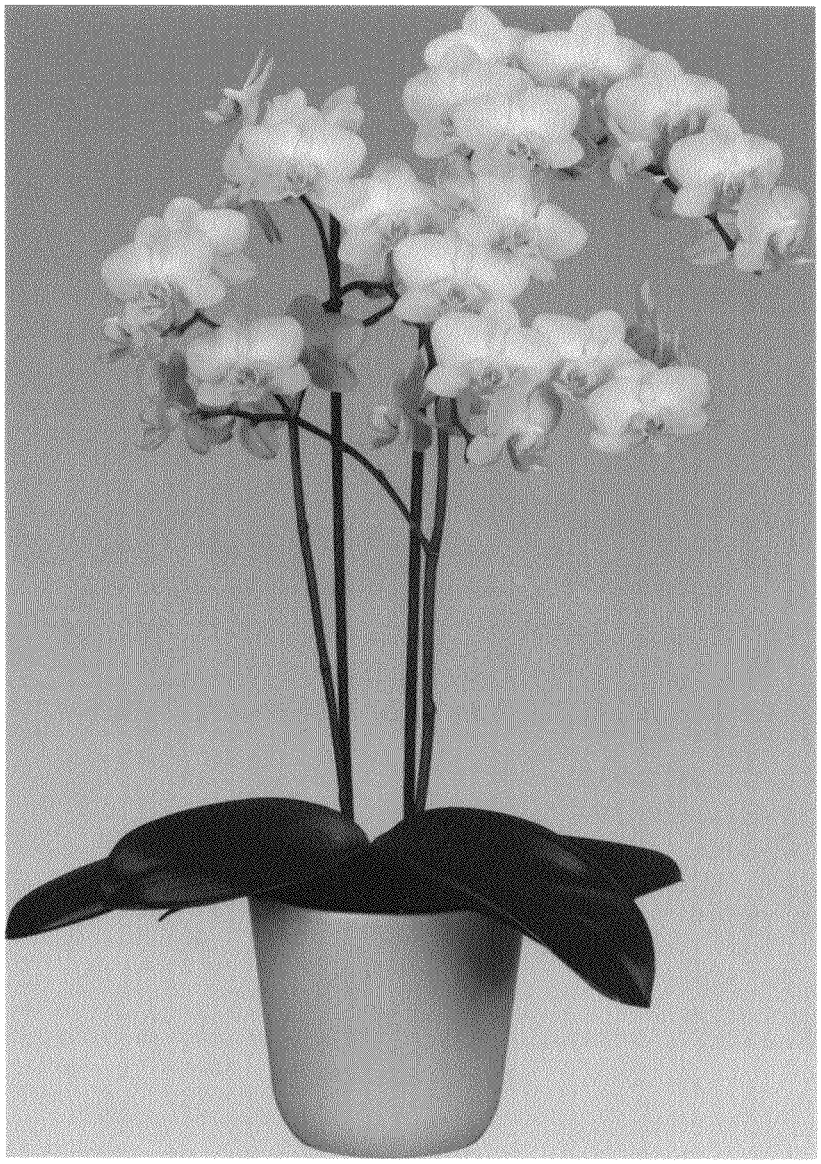
FIG. 1 shows a side view perspective of a typical flowering plant of 'Ventura' in a 12 cm pot, at 16 months of age.

The new *Phalaenopsis* cultivar 'Ventura' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Ventura' as grown in a greenhouse in Strengweg, Heemskerk, The Netherlands, under conditions which closely approximate those generally used in commercial practice. Initially, the ideal temperature to grow plants of 'Ventura' is 27° C. during the day and at night. Then, during the flowering phase of 'Ventura', the ideal growing temperature is 20-22° C. during the day and 18° C. at night. Light levels for growing 'Ventura' are a minimum of 5,000 lux and a maximum of 10,000 lux. A balanced fertilizer with level of 200 ppm N, 87 ppm P, 168 ppm K is applied. Duration of growth of 'Ventura' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Ventura' plants described is 12 months after potting.

Classification:
- *Botanical.*—*Phalaenopsis* hybrid.

Parentage:
- *Female or seed parent.*—*Phalaenopsis* cultivar designated 'Golden Sun', unpatented.
- *Male or pollen parent.*—*Phalaenopsis* cultivar designated 'Sara Lee', unpatented.

Propagation:
- *Type.*—Tissue culture; mericloning.
- *Rooting habit and description.*—Fleshy; approximately 3 mm-6 mm wide and greyed/green in color (RHS 196A); freely branching. It takes 12 weeks for plants growing in tissue culture to initiate roots.

Plant:
- *Size at maturity.*—Height (from bottom of pot to highest flower): about 53 cm. Spread: about 54 cm.
- *Growth habit.*—Small; green (RHS N137A) leaves and a relatively normal raceme.
- *Vigor.*—Moderate.
- *Crop time.*—Following asexual propagation, at about 26 weeks 2 leaves appear; at about 30 weeks 3-4 leaves appear; after a cold treatment of about 4-8 weeks at a temperature of about 19° C. about 2 racemes with flowers appear.

Foliage:
- *Quantity per plant.*—About 6 to 8 leaves are produced before flowering.
- *Arrangement and attachment.*—Half up/horizontal and on two sides.
- *Overall shape of leaf.*—Oval, the tip is blunt and asymmetric.
- *Texture* (*upper & under surface*).—Smooth and leathery.
- *Pubescence.*—None.
- *Mature leaf length.*—About 15 to 20 cm.
- *Mature leaf width.*—About 7 to 9 cm.
- *Mature leaf thickness.*—About 2 mm.
- *Mature leaf color.*—Upper surface: green (RHS N137A). Under surface: yellow/green (RHS 146B).
- *Leaf base.*—Acute.
- *Margin.*—Entire.
- *Venation.*—Pattern: parallel. Color of midvein: upper surface: green (RHS N137A). Under surface: yellow/green (RHS 146B).

Raceme:
- *Quantity per plant.*—About 1 to 2.
- *Number of flowers per raceme.*—About 7 to 20.
- *Length.*—About 45 cm to 60 cm.
- *Diameter.*—About 6 cm.
- *Strength.*—Strong.
- *Aspect.*—Upright.
- *Texture.*—Glabrous and smooth.
- *Color.*—Yellow/green (RHS 146A).
- *Internode.*—Length: about 35 mm to 40 mm.

Inflorescence description:
- *Appearance.*—Upright to slightly pendant, racemose inflorescence with bilaterally symmetrical flowers that open in succession beginning with the lowermost flower.
- *Buds.*—Height (from base to tip): about 15 mm to 21 mm. Diameter (at midpoint): about 15 mm to 20 mm. Shape: egg-shaped/oval. Color: yellow/green (RHS 144C). Orientation: same as flowers (forward facing).
- *Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—Present.

Figure 2:
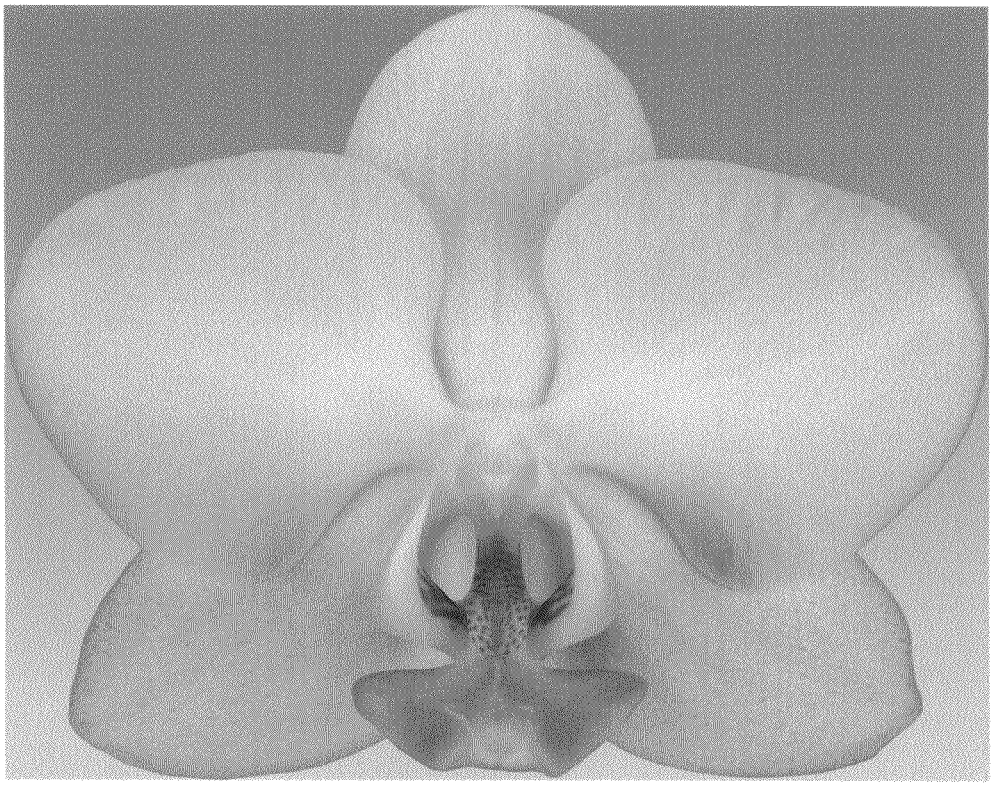
FIG. 2 shows a close-up view of the typical buds and flowers of 'Ventura'.
Figure 3:
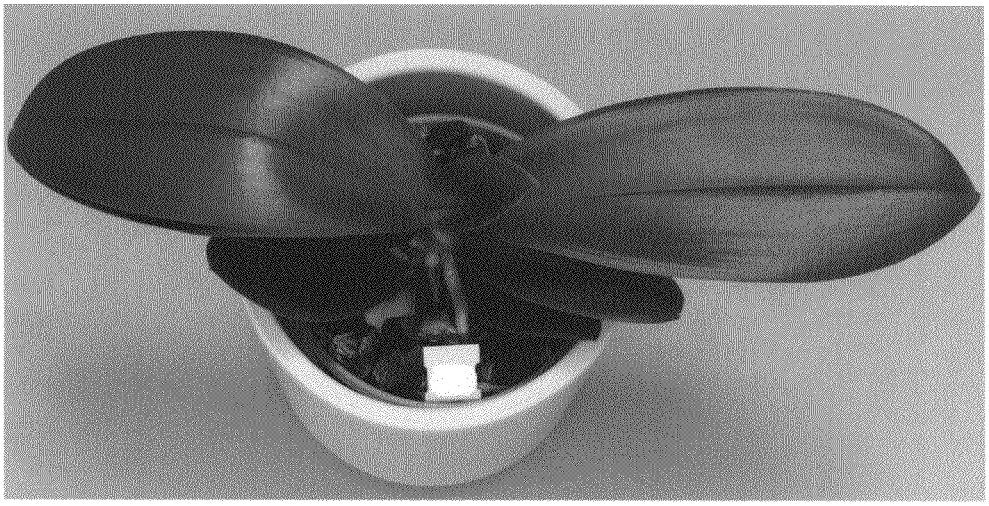
FIG. 3 shows a close-up view of the typical leaves of 'Ventura'.

*Flower*.—Rate of opening: Flowers fully opened about 2 to 3 days after petal and sepal separation. Orientation at opening: slanted upward and outward. Shape: Typical shape of *Phalaenopsis*; see FIG. 2. Size (of single bloom): Height: about 60 mm. Diameter: about 67 mm. Depth of tube: about 15 mm.

*Petals*.—Quantity and arrangement: three petals and three sepals that are trimerous, overlapping and arranged in 2 whorls. Petals are more pronounced than sepals. Arrangement: Inner whorl comprises 3 petals: 2 lateral petals and labellum. 2 lateral petals: Overall shape: broadly ovate and weakly cupped. Apex: oval. Margin: entire and weakly undulate. Base: broadly ovate. Length: about 30 mm. Width: about 30 mm. Texture: Upper surface: smooth and satiny. Under surface: smooth and satiny. Color (when fully opened): upper surface: main color is green/yellow (RHS 1D). At the base a white mark (RHS NN155C). Under surface: main color is green/yellow (RHS 1D) with at the base a little white (RHS NN155C). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Apex: oval. Length: about 20 mm. Width (not flattened): about 19 mm. Texture: Upper and under surface: smooth and satiny. Color (when fully opened): Midlobe, upper surface: yellow (RHS 7A). The end is white (RHS NN155C) and at the base some red/purple stripes and spots (RHS 70A). Under surface: yellow (RHS 7A) with white (RHS NN155C) and at the base red/purple spots (RHS 70B). Lateral lobes, upper surface: yellow (RHS 7A) with a large white mark (RHS NN155C) and red/purple stripes and spots at the base (RHS 70A). Under surface: yellow (RHS 7A) with white (RHS NN155C). At the base some vague red/purple spots (RHS 71A).

*Cirrhi*.—About 6 mm. Color: yellow (RHS 7A). Pestle (Callosities): Length: about 5 mm. Width (not flattened): about 5 mm. Color: yellow (RHS 1A) with red/purple stripes and spots (RHS 70A).

*Sepals*.—Arrangement: Outer whorl comprises 3 sepals. Overall shape: elliptical and weakly cupped. Margin: entire and weakly undulate. Length: about 33 mm. Width: about 22 mm. Apex: oval/round. Texture: Upper and under surface: smooth and satiny. Color (when fully opened): upper surface, dorsal and lateral: main color is green/yellow (RHS 1C). Some white at the base (RHS NN155B). Under surface, dorsal and lateral: green/yellow (RHS 1B and RHS 1C). At the base some white (RHS NN155B).

*Pedicel*.—Length: about 35 to 40 mm. Diameter: about 3 mm. Color: At the flower white (RHS 155C) which runs into yellow/green (RHS 145C) and then yellow/green (RHS 145A).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 16 mm. Diameter: about 5 mm. Color: white (RHS NN155B).

*Pollinia*.—Quantity: Two. Size: about 1 mm. Color: RHS 23A.

*Ovary*.—Length: about 4 mm. Diameter: about 5 mm. Color: white (RHS NN155B).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Ventura', as illustrated and described herein.

* * * * *